United States Patent
Hon (10) Patent No.: US 8,579,890 B2
(45) Date of Patent: Nov. 12, 2013

(54) CRYO-ABLATION REFRIGERANT DISTRIBUTION CATHETER

(75) Inventor: Raphael Hon, Irvine, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1120 days.

(21) Appl. No.: 12/402,970

(22) Filed: Mar. 12, 2009

(65) Prior Publication Data

US 2009/0234345 A1 Sep. 17, 2009

Related U.S. Application Data

(60) Provisional application No. 61/064,577, filed on Mar. 13, 2008.

(51) Int. Cl.
*A61B 18/18* (2006.01)
*A61M 37/00* (2006.01)

(52) U.S. Cl.
USPC ............... 606/20; 606/21; 606/22; 606/23; 604/23

(58) Field of Classification Search
USPC ............ 606/20–23, 25, 26, 24; 604/23
See application file for complete search history.

(56) References Cited

U.S. PATENT DOCUMENTS

| | | | |
|---|---|---|---|
| 5,147,355 A | | 9/1992 | Friedman et al. |
| 6,270,493 B1 * | | 8/2001 | Lalonde et al. .............. 606/23 |
| 6,551,274 B2 | | 4/2003 | Heiner |
| 6,585,728 B2 | | 7/2003 | Heiner et al. |
| 6,796,979 B2 | | 9/2004 | Lentz |
| 6,893,433 B2 | | 5/2005 | Lentz |
| 6,905,493 B2 | | 6/2005 | Lentz |
| 6,905,494 B2 | | 6/2005 | Yon et al. |
| 6,955,673 B2 | | 10/2005 | Lentz |
| 6,981,382 B2 | | 1/2006 | Lentz et al. |
| 7,001,378 B2 | | 2/2006 | Yon et al. |
| 7,104,984 B2 | | 9/2006 | Ryba |
| 7,156,840 B2 | | 1/2007 | Lentz et al. |
| 7,195,625 B2 | | 3/2007 | Lentz |
| 7,288,089 B2 | | 10/2007 | Yon et al. |
| 7,500,973 B2 | | 3/2009 | Vancelette et al. |
| 2002/0026182 A1 | | 2/2002 | Joye et al. |
| 2002/0045894 A1 | | 4/2002 | Joye et al. |
| 2003/0060762 A1 | | 3/2003 | Zvuloni et al. |
| 2005/0027289 A1 | | 2/2005 | Castellano et al. |
| 2005/0283146 A1 | | 12/2005 | Lentz |

FOREIGN PATENT DOCUMENTS

WO WO 2008/000065 1/2008

OTHER PUBLICATIONS

PCT International Search Report and Written Opinion issued by European Patent Office for International Application No. PCT/US2009/036974, mailing date Jul. 23, 2009.

* cited by examiner

*Primary Examiner* — Emily Schmidt
*Assistant Examiner* — Bradley G Thomas, Jr.
(74) *Attorney, Agent, or Firm* — Seager, Tufte & Wickhem, LLC (57) ABSTRACT

Described herein are methods and devices for performing ablation via a cryoablation catheter. An ablation catheter having a cyroablation chamber at its distal end can be used to achieve a uniform ablation band in or around the pulmonary veins. The cyrochamber can house a dispersion member in fluid communication with a refrigerant supply and can function to evenly distribute received refrigerant over some portion of the inner wall of the cryochamber. As a result of this even distribution of refrigerant within the cyrochamber, uniform ablation of the targeted tissue of the patient can be achieved.

23 Claims, 12 Drawing Sheets

SECTION A-A

FIG. 2B

SECTION B-B

CRYO-ABLATION REFRIGERANT DISTRIBUTION CATHETER

This application claims priority to Provisional Application Ser. No. 61/064,577 entitled "Cryo-Ablation Refrigerant Distribution Catheter" filed Mar. 13, 2008, which is incorporated herein by reference.

BACKGROUND OF THE INVENTION

Atrial fibrillation is the most common heart arrhythmia in the world, affecting over 2.5 million people in the United States alone. In fibrillation the upper chambers of the heart, known as the atria, quiver rapidly instead of beating in a steady rhythm. The rapid quivering reduces the heart's ability to properly function as a pump.

The disorder typically increases the risk of acquiring a number of potentially deadly complications, including thrombo-embolic stroke, dilated cardiomyopathy, and congestive heart failure. Quality of life is also impaired by atrial fibrillation symptoms such as palpitations, chest pain, dyspnea, fatigue, and dizziness. People with atrial fibrillation have, on average, a five-fold increase in morbidity and a two-fold increase in mortality compared to people with normal sinus rhythm.

Treatments for atrial fibrillation include drug therapy, electrocardioversion, and surgical or intravascular ablation techniques. Surgical ablation is an invasive procedure whereby the surgeon creates a maze-like pattern of incisions on the inside of the patient's atria. The scarring that results acts to block the abnormal electrical pathways in the heart that lead to atrial fibrillation. Surgical ablation has a much higher success rate than drug therapies and lacks the potential for side effects presented by drug treatment. However, highly invasive (e.g., open-chest) procedures can present substantial risks.

Intravascular ablation similarly creates scar tissue that impedes the travel of errant electrical impulses in the heart tissue. Radio frequency and microwaves are exemplary energy sources for such ablation. Additionally, cryoablation techniques have also been explored.

One benefit of radio frequency, microwave, and cryoablation is the ability to deliver therapy via a catheter. These ablation techniques use a less invasive, transvenous approach. To perform such a procedure, specifically a cryoablation procedure, the tip of a cryoablation catheter is typically inserted into and advanced within the vasculature of a patient until the tip is located adjacent to the targeted tissue. Next, in a typical cryocatheter, a refrigerant is pumped into the catheter for expansion into an expansion chamber that is located at or near the catheter tip. The expansion of the refrigerant cools the catheter tip and target tissue. By cooling the tip of a cryoablation catheter to sub-zero temperatures, the cells in the heart responsible for conducting the arrhythmia are altered so that they no longer conduct electrical impulses. However, in some instances, the refrigerant is not evenly distributed within the desired region of the expansion chamber. This results in the non-uniform or uneven ablation of the targeted tissue.

Accordingly, current treatments for atrial fibrillation could benefit from improved techniques and devices for cyroablating the cells in the heart responsible for conducting cardiac arrhythmias.

SUMMARY OF THE INVENTION

Described herein is a cryoablation catheter for use in tissue ablation. The catheter comprises an elongate supply lumen, or catheter body, which carries a cryofluid or refrigerant from a refrigerant supply unit. Generally, a source of refrigerant is connected to the proximal end of the supply lumen and the cryochamber, or expansion chamber, is located at the lumen's distal end. The ablation catheter also comprises a refrigerant dispersion member. The dispersion member, located near the distal end of the supply lumen, is at least partially housed by the expansion chamber and serves to evenly distribute the refrigerant exiting the distal end of the supply lumen across at least some portion of the interior of the expansion chamber. An even distribution of cryofluid can facilitate proper ablation procedures by reducing the risk of inconsistent cooling of the targeted tissue in contact with the ablation catheter tip.

In one aspect, the catheter described herein can be used for performing ablation near or within the pulmonary veins of the heart where a uniform circumferential ablation band across the targeted tissue is desired. However, the devices described herein are not limited to cardiac applications.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF EXEMPLARY EMBODIMENTS

Disclosed herein are various embodiments of a cryoablation catheter device. Generally, the device allows an operator to cool tissue targeted for ablation in a consistent and/or uniform fashion. As part of various procedures, where ablation is to be performed in or around the pulmonary veins, it may be desirable to evenly cool the tissue in a circumferential band. Cryoablation catheters known in the art, in which refrigerant is simply released into the cryochamber, can result in an uneven distribution of cryofluid on a desired region of the interior wall of the cryochamber or uneven cooling of the targeted tissue. This, in turn, can necessitate additional ablations and extend procedure duration. The cyroablation catheter disclosed below solves this problem by positioning a dispersion member or dispersion body within the cyrochamber. In one aspect, the dispersion member serves to direct the cryofluid towards the interior wall of the expansion chamber in such a way as to ensure even distribution of the cryofluid over the desired area of the expansion chamber and/or even cooling of the targeted tissue. This can result in reliable and uniform ablation of the surrounding tissue.

While the ablation devices described herein focus on epicardial ablation, one skilled in the art will appreciate that the catheter devices, systems, and methods of use described below can permit ablation of a variety of anatomic structures. In one aspect, a cyroablation catheter is sized and shaped for ablating cardiac tissue. In another aspect, the catheter is configured specifically for ablation at the ostium of the pulmonary veins or surrounding tissue. However, the methods and devices described herein can be used for other, non-cardiac procedures.

Reference will now be made in detail to the exemplary embodiments of the invention, examples of which are illustrated in the accompanying drawings. Wherever possible, the same reference numbers will be used throughout the drawings to refer to the same or like parts.

Figure 1:
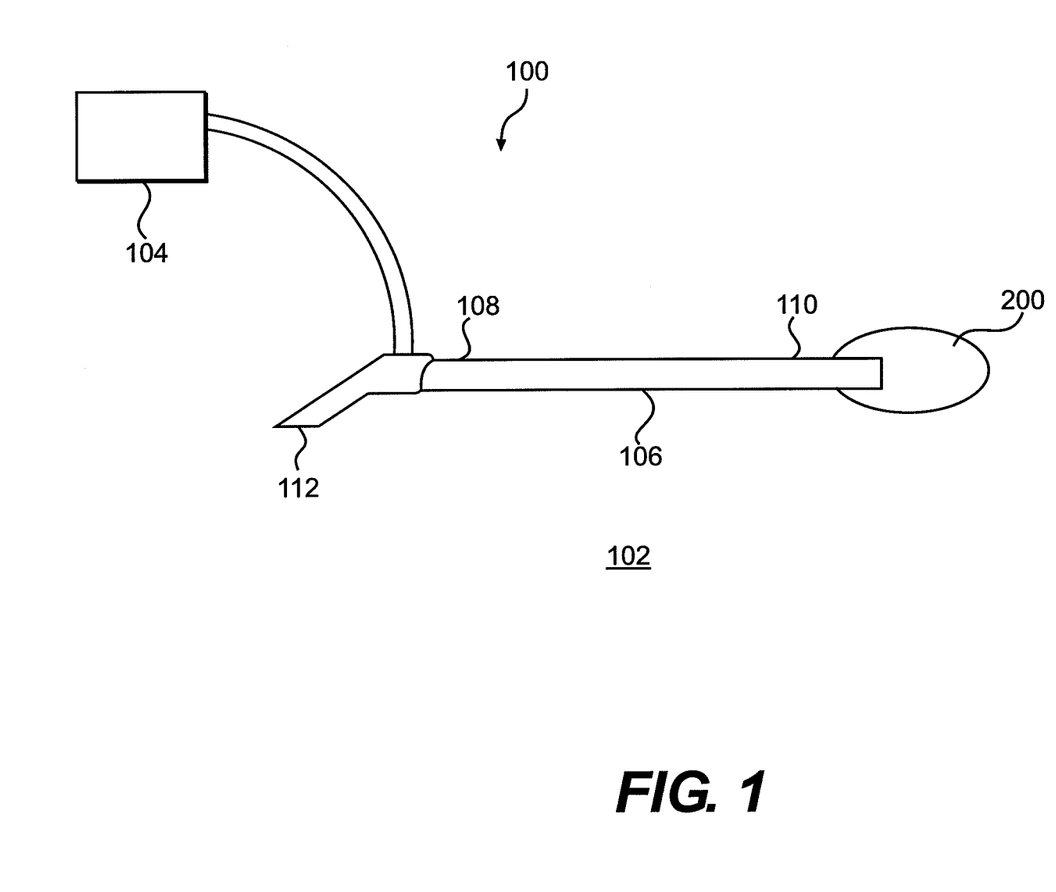
FIG. 1 is a side view of one embodiment of a cryoablation system disclosed herein.

FIG. 1 illustrates one exemplary embodiment of a cyroablation system 100 for ablating tissue with cryofluid comprising an ablation device 102 and a cyrofluid or refrigerant supply unit 104. In one aspect, device 102 can include an elongate catheter body 106 extending between proximal and distal ends 108 and 110, respectively. An expandable member 200, into which cyrofluid can be placed as will be discussed in more detail below, can be coupled with distal end 108 of elongate catheter body 106 such that the expandable member and the catheter body are in fluid communication.

In one aspect, catheter body 106 can be defined by a flexible or rigid body having one or more channels through which treatment fluids can be delivered. For example, catheter body 106 can include at least one lumen for the delivery of a cryofluid and/or at least one lumen for the exhaust of spent refrigerant. In addition, wires for conducting therapeutic energy and/or for sending/receiving sensed signals can extend along at least a portion of catheter body 106.

The catheter body can also include a variety of features to facilitate insertion and/or placement of expandable member 200 relative to target tissue. In one embodiment, device 102 can include an articulating segment defined by a portion of catheter body 106. For example, a distal portion of body 106 can be actuated by a user from a proximal location to steer expandable body into a target location. In one exemplary aspect, catheter body 106 can include push and/or pull strands to transmit forces to the articulation segment.

The size and shape of catheter body 106 can be chosen based on the intended use of device 102. Where device 102 is used for cardiac ablation, catheter body 106 can be sized and shaped for insertion through a vascular lumen. In addition, the materials and structure of catheter body 106 can be chosen to provide a flexible elongated body. One skilled in the art will appreciate that catheter body 106 can represent the variety of catheter structures commonly known in the art for a vascular approach. However, the devices described herein need not be delivered via a transvenous route and/or the target tissue need not be cardiac tissue.

A user interface or handle 112 can be coupled to proximal end 108 of catheter body 106, permitting a clinician to grasp device 102. Handle 112 can have a variety of forms depending on the intended use of device 102 and/or the environment in which device 102 is used. In one aspect, handle 112 can include one or more sources of liquid or gas for expanding expandable member 200. Controls for governing the delivery of liquid, such as a cryofluid or volume displacement fluid, can, in one aspect, also be located on handle 112. Alternatively, or additionally, handle 112 can be configured to mate with one or more sources of liquid such as refrigerant supply unit 104. In one embodiment, supply unit 104 includes a cryofluid and/or volume displacement fluid. Additionally, supply unit 104 can maintain the cryofluid under high pressure. Among those fluids commonly used for cyroablation are liquid nitrous oxide, liquid carbon dioxide, and/or fluorocarbons, but any other gas, fluid, or refrigerant known in the art can also be used. In another aspect, supply unit 104 can further include a mechanism for regulating and controlling expansion of expandable member 200 via delivery of fluid.

Figure 2A:
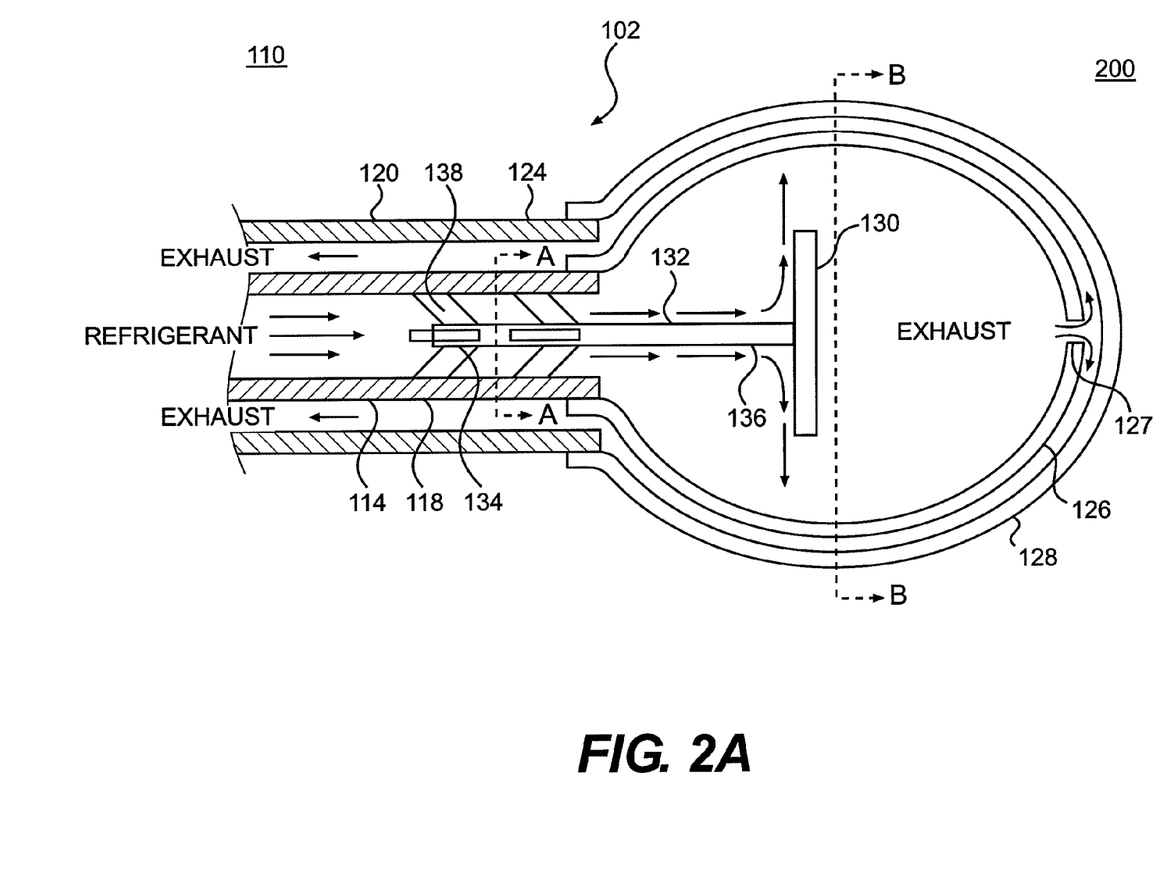
FIG. 2A is a cross-sectional side view of one embodiment of a cryoablation catheter disclosed herein.

Referring now to FIG. 2A, one exemplary embodiment of cyroablation catheter 102 is shown. Specifically, distal end 110 of catheter body 106 and expandable member 200 are depicted. In one aspect, catheter body 106 can be comprised of a supply lumen 114, having a proximal end 116 (not pictured) and a distal end 118, and an exhaust lumen 120, having a proximal end 122 (not pictured) and a distal end 124. In one embodiment, the supply lumen and the exhaust lumen can be concentrically positioned, the supply lumen residing within the exhaust lumen. In other embodiments, however, this may not be the case. For example, in another embodiment, the exhaust lumen may reside within the supply lumen or the two lumens could be positioned side by side. Further, in other embodiments, there can be additional lumens serving other functions, such as providing a volume displacement fluid, separate from the cyrofluid, to expandable member 200.

In another aspect of the embodiment depicted, expandable member 200 can be comprised of a cyrochamber 126 housed within an exhaust chamber 128. These expandable chambers or balloons can be comprised of any suitable material commonly used in the art. In one embodiment, cyrochamber 126 and exhaust chamber 128 can be comprised of a polyurethane. In other embodiments, however, they can be comprised of another material. In some embodiments, the chambers can be rigid structures comprised of a non-expandable material. Additionally, in different embodiments, there can be an additional balloon or chamber that houses exhaust chamber 128. This additional balloon can serve to protect the patient should a rupture in the cryochamber and/or exhaust chamber occur.

Again referring to FIG. 2A, in another aspect, cryochamber 126 can be coupled to, and in fluid communication with, distal end 118 of supply lumen 114. Similarly, exhaust chamber 128 can be coupled to, and in fluid communication with, distal end 124 of exhaust lumen 120. These couplings can be airtight and achieved in various ways. For example, in one embodiment, cyrochamber 126 and/or exhaust chamber 128 can be adhesively coupled to the distal ends of the catheter lumens. In another embodiment, the chambers can be mechanically mated to the distal ends of the lumens. For example, the chambers can be threadedly or frictionally mated to the lumens. Alternatively, the chambers and the lumens could be integrated such that they are a single piece. Other embodiments may incorporate different methods of fastening the chambers to the distal ends of the lumens.

Figure 2B:
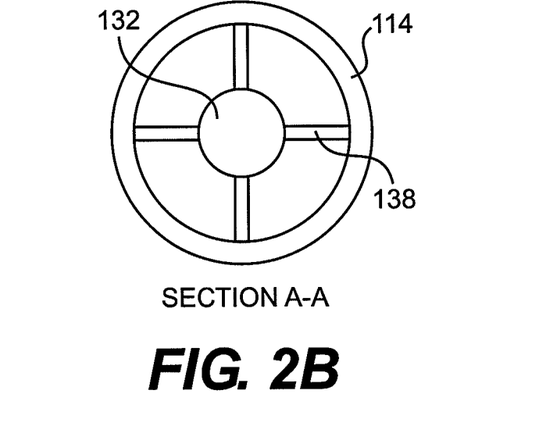
FIG. 2B is a cross-sectional front view of one embodiment of a cryoablation catheter disclosed herein.

A dispersion member 130 can reside within cyrochamber 126. In the embodiment depicted, dispersion member 130 resembles a plate-like member, circular in a plane parallel to cross-section B-B and having a relatively flat surface facing distal end 118 of supply lumen 114. As discussed below, however, in other embodiments, the shape of dispersion member 130, particularly the shape of the surface facing the distal end of supply lumen 114, can depend on the desired flow of the refrigerant within cyrochamber 126. For example, in other embodiments, dispersion member 130 can be conically or pyramidally shaped. In other embodiments, the surface of dispersion member 130 facing the distal end of supply lumen 114 can be convex or concave in shape. Alternative embodiments can comprise dispersion members of other various shapes.

In one aspect, the dispersion member can be mated and/or coupled to one of the catheter lumens so as to anchor the dispersion member within the cyrochamber. For example, the dispersion member can be mated to the inner surface of the supply lumen in such a way as to still allow passage of the refrigerant.

In the embodiment depicted, dispersion member 130 can be anchored in place within cyrochamber 126 through the use of stem 132 having a proximal end 134 and a distal end 136. In one aspect, distal end 136 of stem 132 can be coupled to dispersion member 130 while the proximal end 134 at least partially resides within distal end 118 or supply lumen 114. Protruding from distal end 136 of stem 132 can be fins 138 which contact the inner surface of supply lumen 114. In one aspect, fins 138 allow stem 132 to be positioned within a central portion of lumen 114. For example, stem 132 can extend along the central axis of lumen 114. In use, cryofluid can flow around the full circumference of stem 132.

In one embodiment, fins 138 can be affixed to the inner surface of lumen 114 using adhesive. In other embodiments, the fins and the supply lumen, along with stem 132 and dispersion member 130, can be manufactured as one piece. For clarity, FIG. 2B, depicting cross-section A-A, provides a front view of stem 132, fins 138, and supply lumen 114. However, this is but one method of securing dispersion member 130 within cyrochamber 126. Various other methods of anchoring dispersion member 130 within the cyrochamber can be incorporated in alternative embodiments.

In practice, a pressurized refrigerant or cyrofluid can be released from refrigerant supply unit 104, enter proximal end 116 of supply lumen 114, flow down to distal end 118 of the lumen, past fins 138 and into cyrochamber 126. Upon entering the cryochamber, the fluid can deflect off of dispersion member 130 configured to divert the fluid toward the inner wall of the chamber. Upon contact with the inner surface of chamber 126, the fluid can begin to "boil," or change into a gaseous state, as it absorbs heat from tissue in contact with the outer surface of expandable member 200. The deflection of the cyrofluid by dispersion member 130 can concentrate the refrigerant stream along a circumferential band around the inner diameter of cyrochamber 126.

Figure 2C:
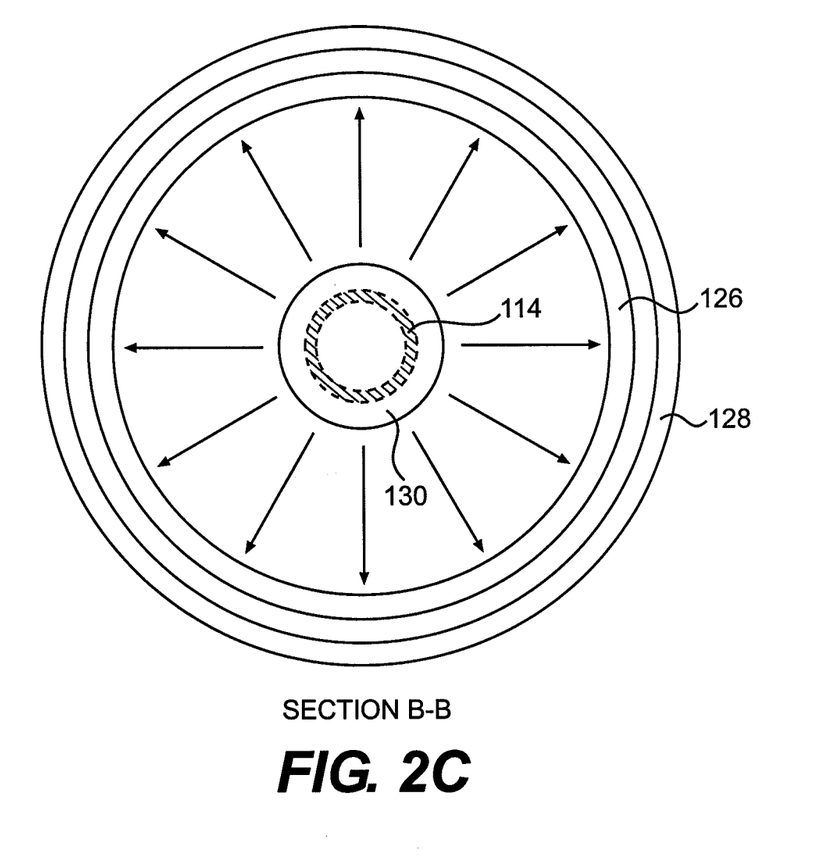
FIG. 2C is a cross-sectional front view of one embodiment of a cryoablation catheter disclosed herein.

FIG. 2C depicts this deflection from a front view. As the refrigerant exits distal end 118 of supply lumen 114 and strikes dispersion member 130, the fluid can deflect off the dispersion member in a radial direction and be directed towards the inner wall of cyrochamber 126. The uniform distribution of the refrigerant in this fashion can facilitate a consistent concentration of refrigerant at a circumferential band within the cyrochamber and result in a uniform ablation band at the targeted tissue.

In another aspect, the spent, or gaseous, refrigerant can then leave cyrochamber 126 through exit 127. In the embodiment depicted in FIG. 2A, exit 127 is located at the distal end of the cyrochamber. The cryofluid can travel between the outer surface of cyrochamber 126 and the inner surface of exhaust chamber 128, towards the chambers proximal ends. The spent cryofluid can then flow into distal end 124 of exhaust lumen 120 and exit the system at proximal end 122 of the lumen. It should be noted, however, the exhaust of spent refrigerant can be accomplished in various ways. Additional methods of exhausting the gas are described below, though other methods can also be incorporated in different embodiments and the methods described herein should not be considered exhaustive.

Figure 3A:
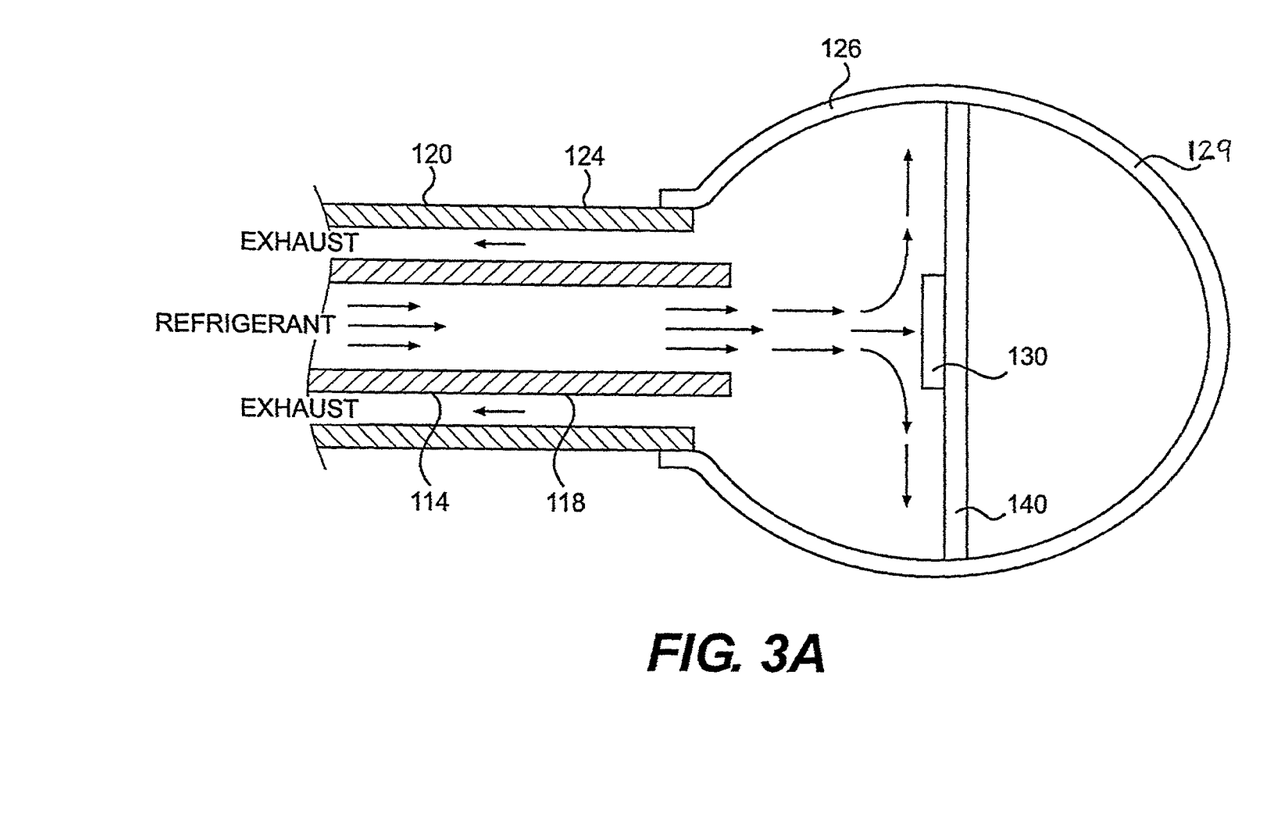
FIG. 3A is a side view of one embodiment of a cryoablation catheter disclosed herein.

Referring now to FIG. 3A, another method of anchoring dispersion member 130 within cyrochamber 126 is depicted. In one aspect, cyrochamber 126 can be subdivided by wall 140. In one embodiment, wall 140 can be comprised of the same material as cyrochamber 126. In other embodiments, wall 140 can be comprised of a more rigid material. For example, wall 140 can be comprised of the same material as dispersion member 130 or the two bodies, the dispersion member and the wall, can be integrated such that wall 140, in and of itself, functions as the dispersion member and serves to divert refrigerant flow towards the inner wall of cyrochamber 126.

In one embodiment, wall 140 can be a collapsible or foldable structure capable of taking on a predetermined shape when an adjacent chamber is pressurized. For example, chamber 129, adjacent cyrochamber 126, can be pressurized to provide support to wall 140 and/or dispersion member 130. Alternatively, wall 140 can be porous such that cyrochamber 126 and chamber 129 can be pressurized concurrently in order to support wall 140 and/or dispersion member 130. In another aspect, the axial location of dispersion member 130 can be altered by changing the shape or position of wall 140 within the cyrochamber. For example, FIG. 3A depicts wall 140 at approximately the middle of cryochamber 126. This can result in the refrigerant flow being diverted at that same axial position and forming an even refrigerant distribution band around the inner diameter of the cryochamber just proximate to wall 140. Alternatively, wall 140 can be located at the distal or proximate ends of the cryochamber, resulting in a corresponding repositioning of the refrigerant distribution band within the chamber.

Figure 3B:
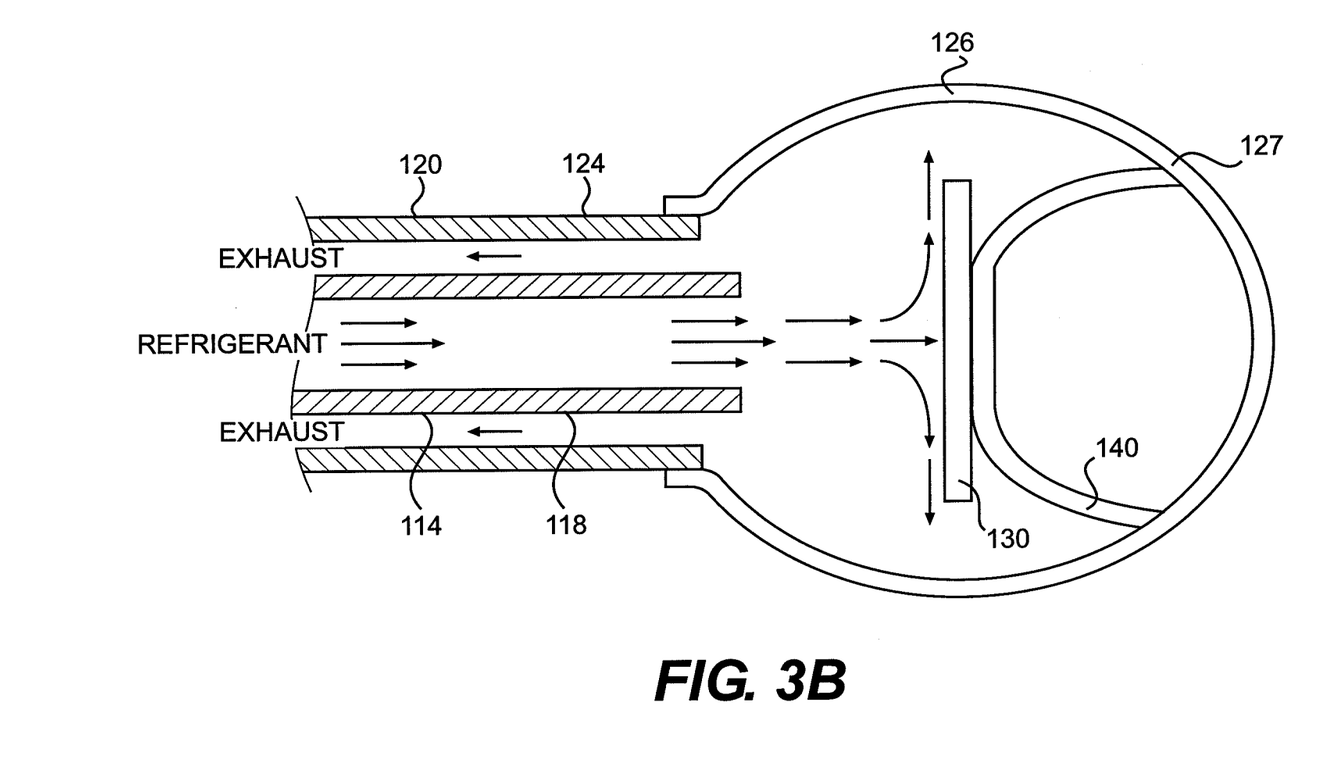
FIG. 3B is a cross-sectional side view of one embodiment of a cryoablation catheter disclosed herein.

FIG. 3B depicts an alternative shape for wall 140. In this embodiment, the wall spans less than the expandable chamber's entire diameter. As a result, wall 140 can be comprised of a non-collapsible rigid material while remaining small enough to traverse a patient's vasculature. Alternatively, wall 140 can be collapsible or foldable, such that is takes on a predetermined shape when cyrochamber 126 is pressurized. Regardless, chamber 129 can be expanded or constructed to adjust the position of wall 140.

FIGS. 3A and 3B also depict an alternative flow path for spent refrigerant from that depicted in FIG. 2A. In the embodiment depicted in FIGS. 3A and 3B, cyrochamber 126 can be coupled to exhaust lumen 120 at its distal end 124. This coupling can be achieved according to methods similar to those described above for coupling the cyrochamber to the supply lumen. Supply lumen 114 can then be positioned concentrically within exhaust lumen such that both distal end 118 of the supply lumen and distal end 124 of the exhaust lumen are in fluid communication with the cyrochamber.

Thus, in operation, refrigerant can be supplied to the cryochamber through the supply lumen and dispersion member 130 can deflect the refrigerant towards the inner wall of the chamber. The fluid deflection can provide a circumferential band of fluid around the inner diameter of the cryochamber resulting in a uniform ablation band at the targeted tissue. Upon absorption of heat, the refrigerant can become a gas and can flow into distal end 124 of exhaust lumen 120 and out of the system. As mentioned above, however, there are other methods of allowing spent refrigerant to exit the cyrochamber.

Figure 4A:
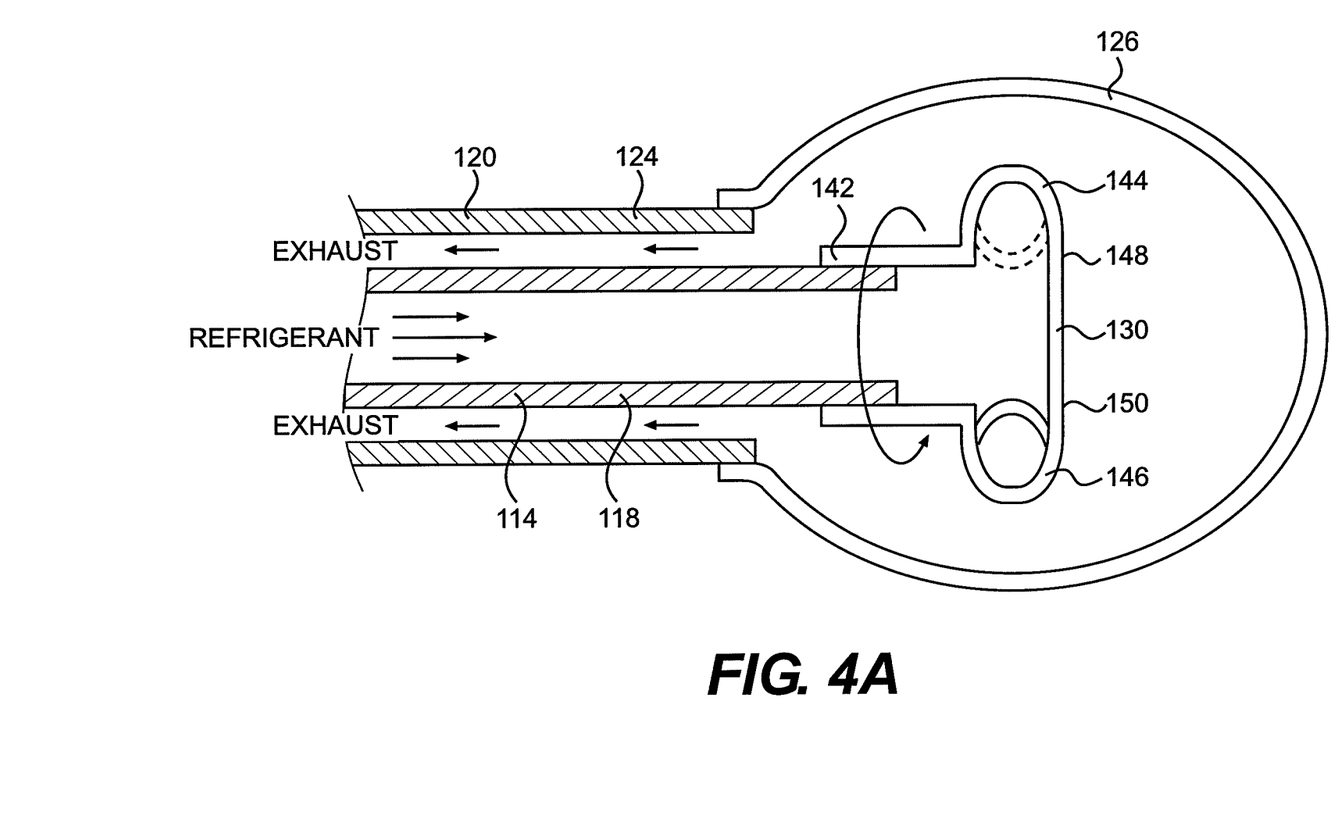
FIG. 4A is a cross-sectional side view of one embodiment of a cryoablation catheter disclosed herein.

Referring now to FIG. 4A, another embodiment of the cyroablation catheter is depicted. In one aspect, the cyroablation catheter depicted can comprise a dispersion member 130 with a flow path therethrough. In one aspect, the movement of fluid through the dispersion member can cause at least a portion of the dispersion member to rotate and distribute cryofluid. FIG. 4A illustrates a rotary dispersion member 130 including a proximal opening 142 and two distal openings 144 and 146. Openings 144 and 146 can be positioned proximate to the outermost ends of radially spaced arms 148 and 150, respectively. The flow path through distal arms 148 and 150, as well as distal openings 144 and 146, can be positioned so as to redirect the refrigerant entering the dispersion member at proximal opening 142 at various angles with respect to the flow exiting the supply lumen. In the embodiment depicted, this can be accomplished using substantially U-shaped distal arms extending from dispersion member 130. In other embodiments, however, distal arms 148 and 150 and openings 142 and 144 can be configured so as to redirect refrigerant flow at some other angle with respect to the fluid entering the dispersion member, depending on the distribution of refrigerant desired.

Figure 4B:
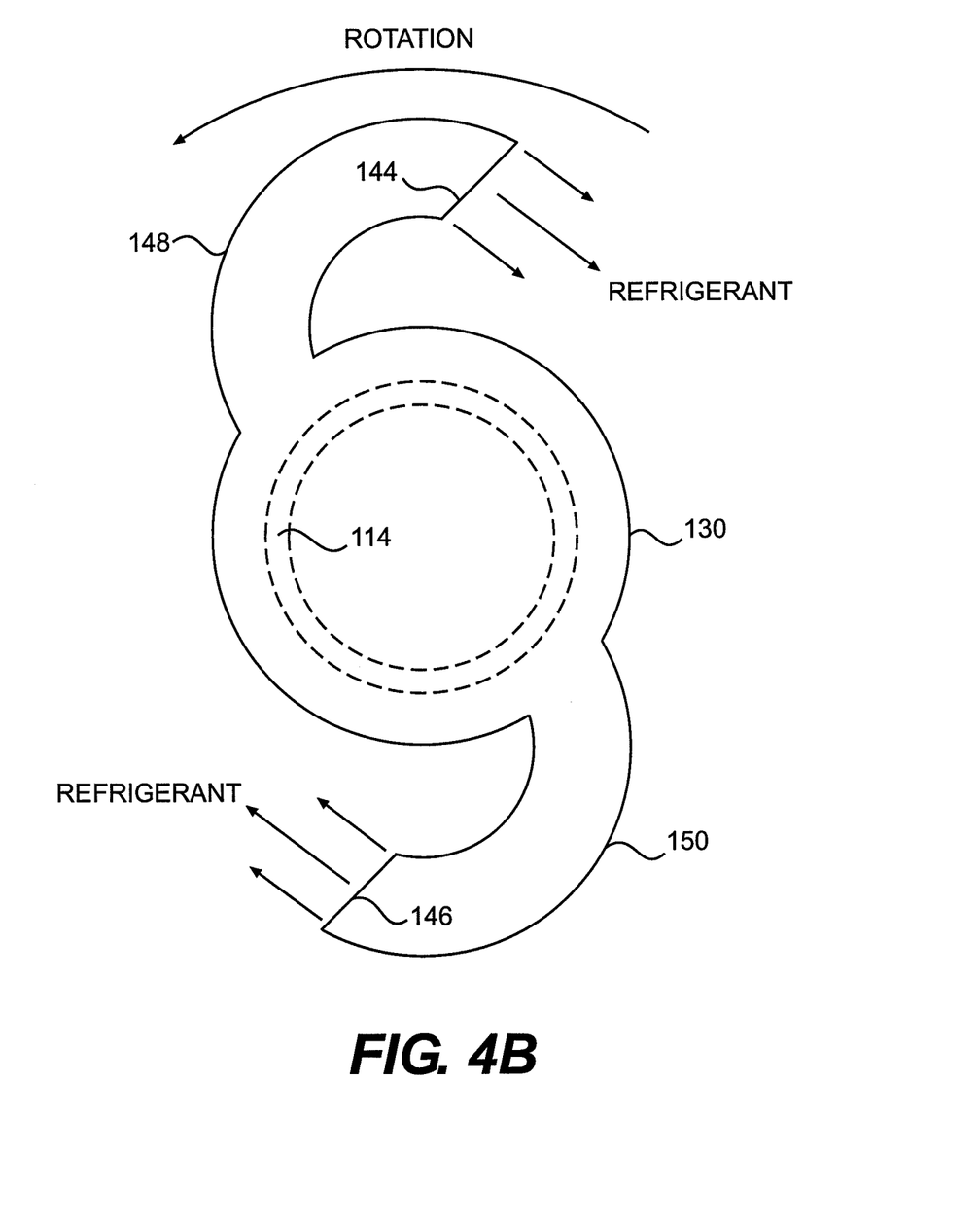
FIG. 4B is a cross-sectional side view of one embodiment of a cryoablation catheter disclosed herein.

Dispersion member 130 can be rotatably coupled to distal end 118 of supply lumen 114. This coupling can be accomplished in various ways, including, but not limited to, a slot and groove connection. Additionally, distal openings 144 and 146 can be configured so as to redirect flow in opposing directions. In this manner, when refrigerant exits supply lumen 114 and enters dispersion member 130 through proximal opening 142, the cyrofluid can be redirected through distal openings 144 and 146. As a result of the rotatable coupling and the shape of distal arms 148 and 150, the forces resulting from the refrigerant exiting the distal openings of the dispersion member can propel the dispersion member and cause it to spin, distributing the exiting fluid in a uniform circumferential band along the inner wall of cyrochamber 126. For clarity, the rotation of dispersion member 130 and the distribution of the refrigerant is depicted in FIG. 4B.

Alternative embodiments can incorporate fewer or additional radially spaced distal openings in dispersion member 130, depending on the desired distribution of cyrofluid within cyrochamber 126. For example, dispersion member 130 can comprise only one distal opening or it can comprise three or more distal openings. Additionally, while the dispersion member depicted in FIG. 4A has circular distal openings, other embodiments can incorporate differently shaped openings. For example, distal openings 144 and 146 can have a slot-like shape in order to achieve a desired pattern of distributed refrigerant or the openings can be configured as narrowing nozzles if a higher velocity flow from the dispersion member is preferred. Additionally, distal arms 148 and 150 can have a different shape in order to alter the reactive forces of the exiting refrigerant or otherwise alter the resulting refrigerant distribution.

Figure 5A:
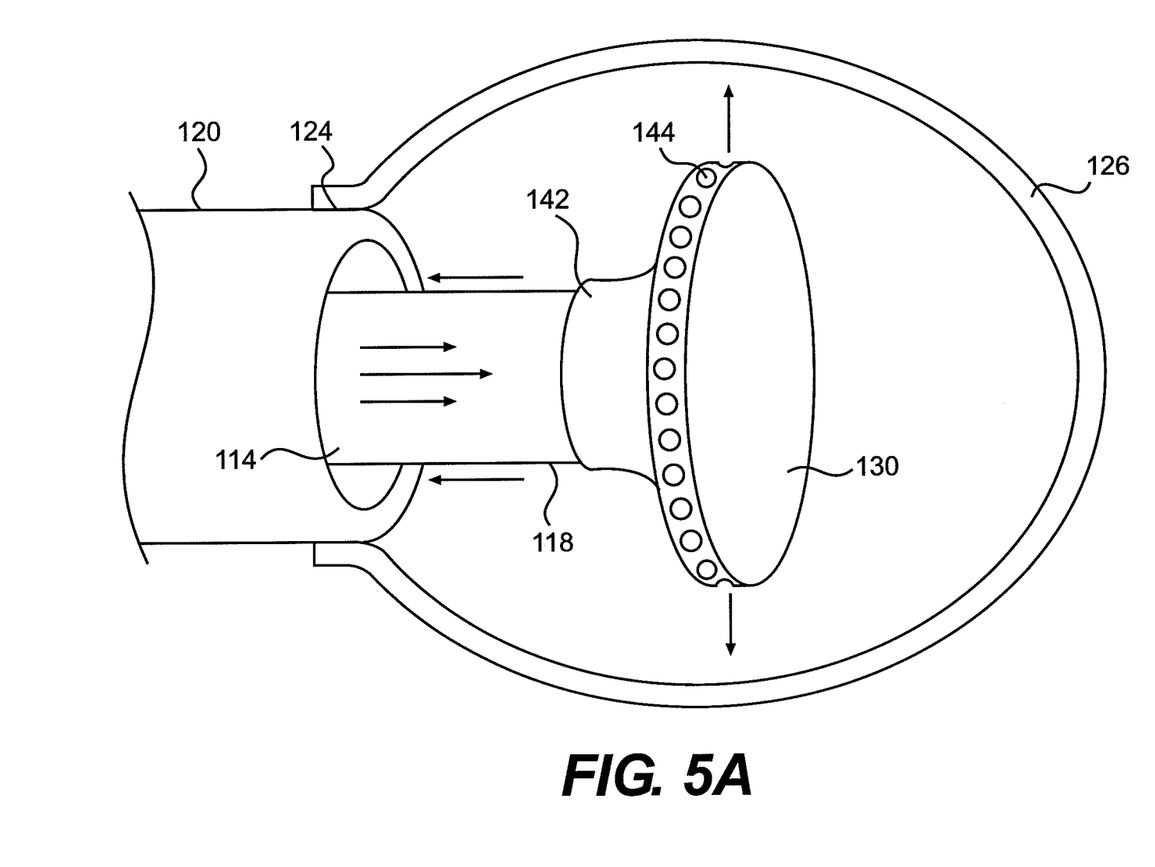
FIG. 5A is a cross-sectional side view of one embodiment of a cryoablation catheter disclosed herein.
Figure 5B:
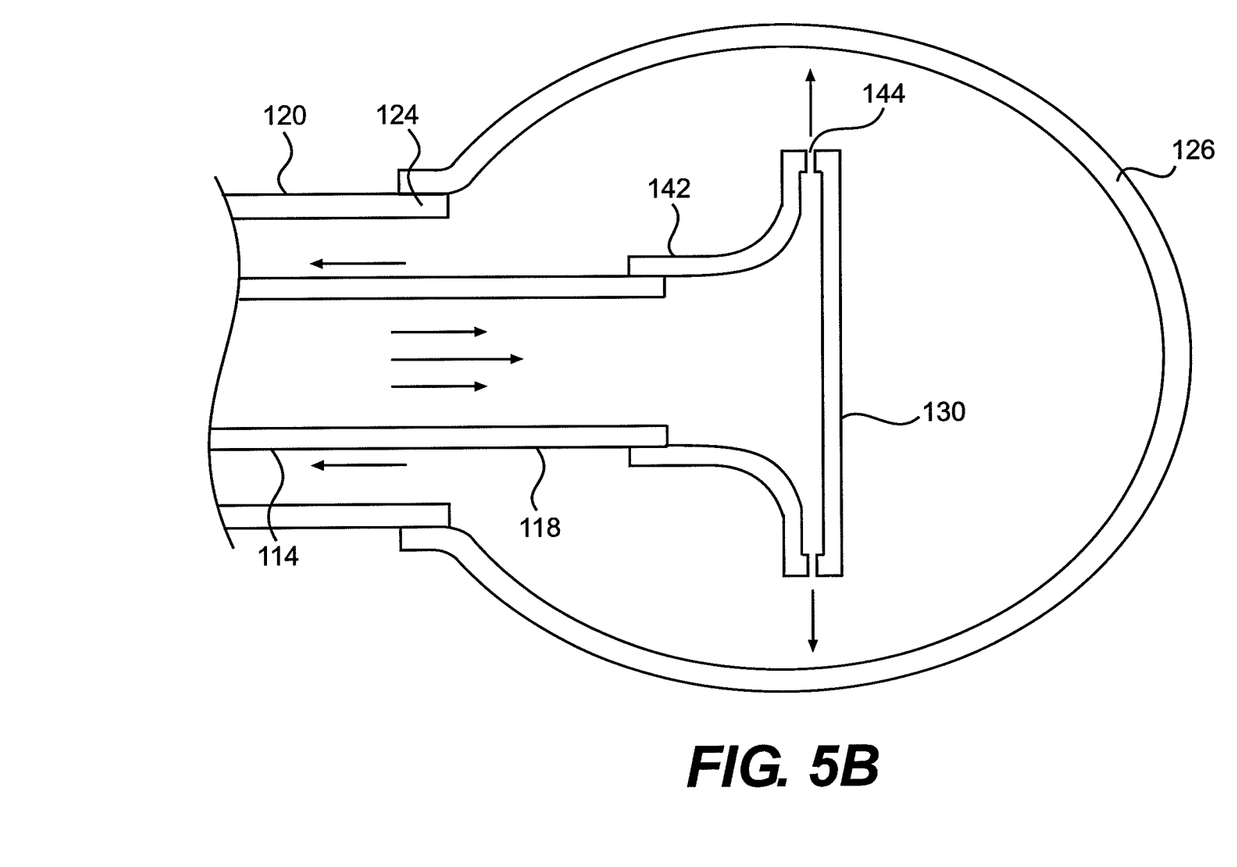
FIG. 5B is a front view of one embodiment of a cryoablation catheter disclosed herein.

FIGS. 5A and 5B depict another embodiment of the invention. As illustrated, dispersion member 130 does not move in response to fluid flow therethrough. Dispersion member 130 has a proximal opening 142 coupled to distal end 118 of supply lumen 114 and tapering outward to a larger disc-like shape at its distal end. The distal end of dispersion member 130 can be closed with the exception of a row of apertures 144 located around its outer circumference. In other embodiments, dispersion member 130 need not taper out to a disc-shape. For example, the distal end of the dispersion member can have a rectangular or cubic shape.

In another aspect, the proximal end of cyrochamber 126 can be coupled to exhaust lumen 120 in a manner previously described. Supply lumen 114 can be concentric with exhaust lumen 120 and positioned within it.

In this embodiment, the cryofluid can exit the supply lumen, enter the proximal end of dispersion member 130 and be redirected out the plurality of apertures toward a circumferential band on the inner wall of cryochamber 126.

In another aspect, apertures 144 are cylindrical, but other embodiments can incorporate openings of a different shape. For example, apertures 144 can be in the shape of a slot. Alternatively, the apertures can be narrowing as they approach the outer surface of dispersion member 130, thereby increasing the velocity of the refrigerant flowing therefrom. Further, other designs can incorporate additional rows of apertures or more or fewer apertures than depicted in FIGS. 5A and 5B. Other embodiments can incorporate apertures that approach the outer surface of dispersion member 130 at an angle, other than being substantially in the radial direction. Additionally, the axial location of the dispersion member can be adjusted depending on the desired distribution of refrigerant.

Figure 6A:
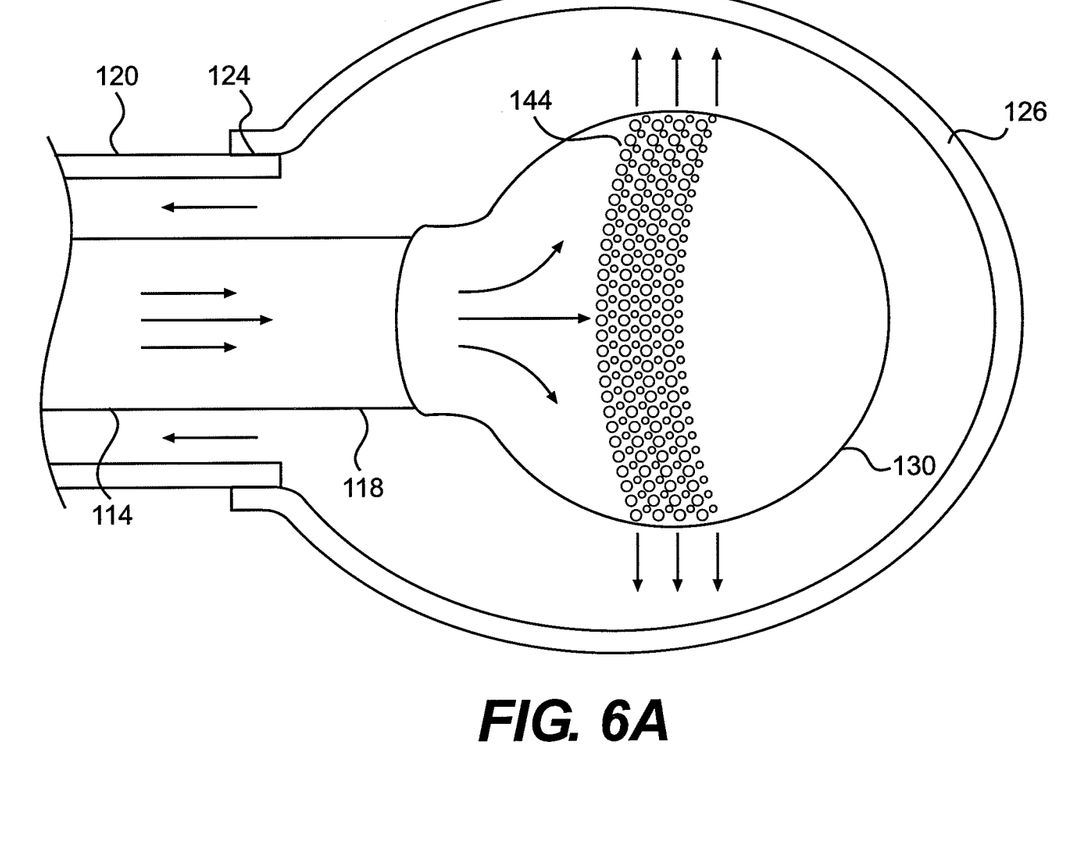
FIG. 6A is a side view of one embodiment of a cryoablation catheter disclosed herein.
Figure 6B:
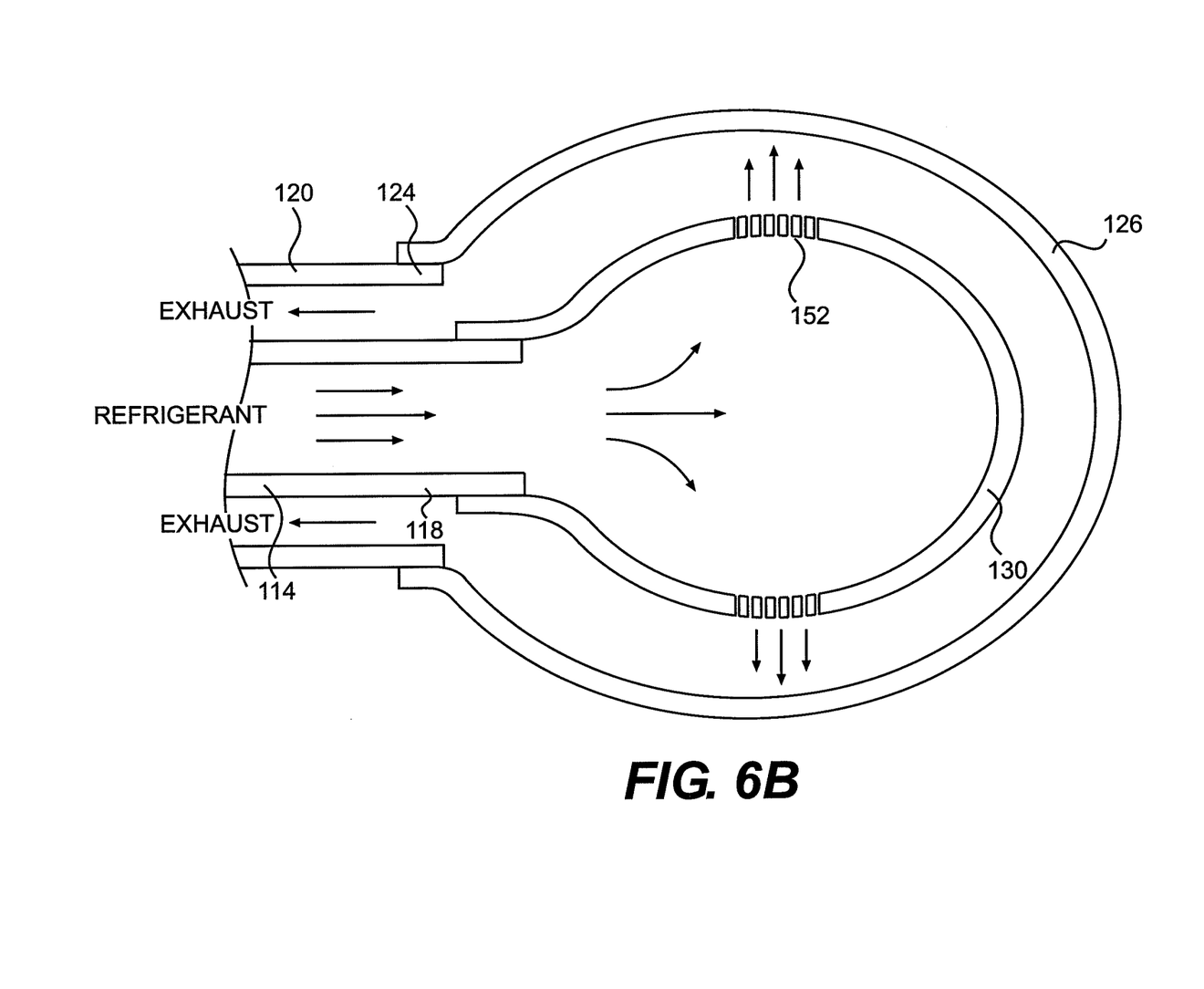
FIG. 6B is a cross-sectional side view of one embodiment of a cryoablation catheter disclosed herein.

Referring now to FIGS. 6A and 6B, another embodiment of the cryoablation catheter is depicted. In one aspect, dispersion member 130 can be comprised of an expandable balloon similar to that of cyrochamber 126. These balloons can be comprised of a polyurethane or any other material commonly used in the art. Alternatively, dispersion member 130 can be comprised of a rigid material. Additionally, although dispersion member 130 is depicted as spherical or substantially spherical in FIG. 6A, member 130 can also take on various other shapes. For example, in another embodiment, the chamber of dispersion member 130 can be cubically, or substantially cubically, shaped.

In one aspect, dispersion member 130 can exhibit a plurality of apertures 144 in a circumferential band around its diameter. In the embodiment depicted, this band of apertures is located at the dispersion member's approximate axial midpoint. However, in other embodiments, this band can be located more proximate or more distal than depicted.

In practice, refrigerant exiting supply lumen 114 can enter dispersion member 130 and, as a result of the pressure in the dispersion member, can be ejected through apertures 144 and directed toward a circumferential band on the inner wall of cyrochamber 126. This can result in the even distribution of the refrigerant about a desired surface of the cyrochamber, corresponding to apertures 144 in the dispersion member. Further, although apertures 144 are depicted as cylindrical openings in the dispersion member, the apertures can be altered in various ways in order to effect a change in the distribution of the refrigerant within the cryochamber. For example, apertures 144 can be shaped as nozzles narrowing from the inner surface of dispersion member 130 to the outer surface of the dispersion member if a higher velocity of refrigerant flow within cyrochamber 126 is desired. Alternatively, apertures 144 can be shaped as slots, rather than cylinders, if a wider distribution at the inner surface of the cyrochamber is desired. Additionally, the apertures can be shaped differently from one another as opposed to all being of one uniform shape. Various other configurations can also be envisioned.

In another aspect of this embodiment, while apertures 144 are depicted as encircling dispersion member 130, the apertures can be located on less than 360° of the dispersion member. For example, if, rather than a continuous ablation band around the full circumference of the adjacent tissue, one desired to ablate only a portion of the circumference of the targeted tissue, apertures 144 can be located across only a portion of dispersion member 130. For example, apertures 144 could be located across only 180°, 90°, or some other portion of the dispersion member.

Similarly, with respect to the embodiments depicted in FIGS. 2A-5B, dispersion member 130 can be configured to dispense cyrofluid along only a portion of the full circumference of the cyrochamber.

Figure 7:
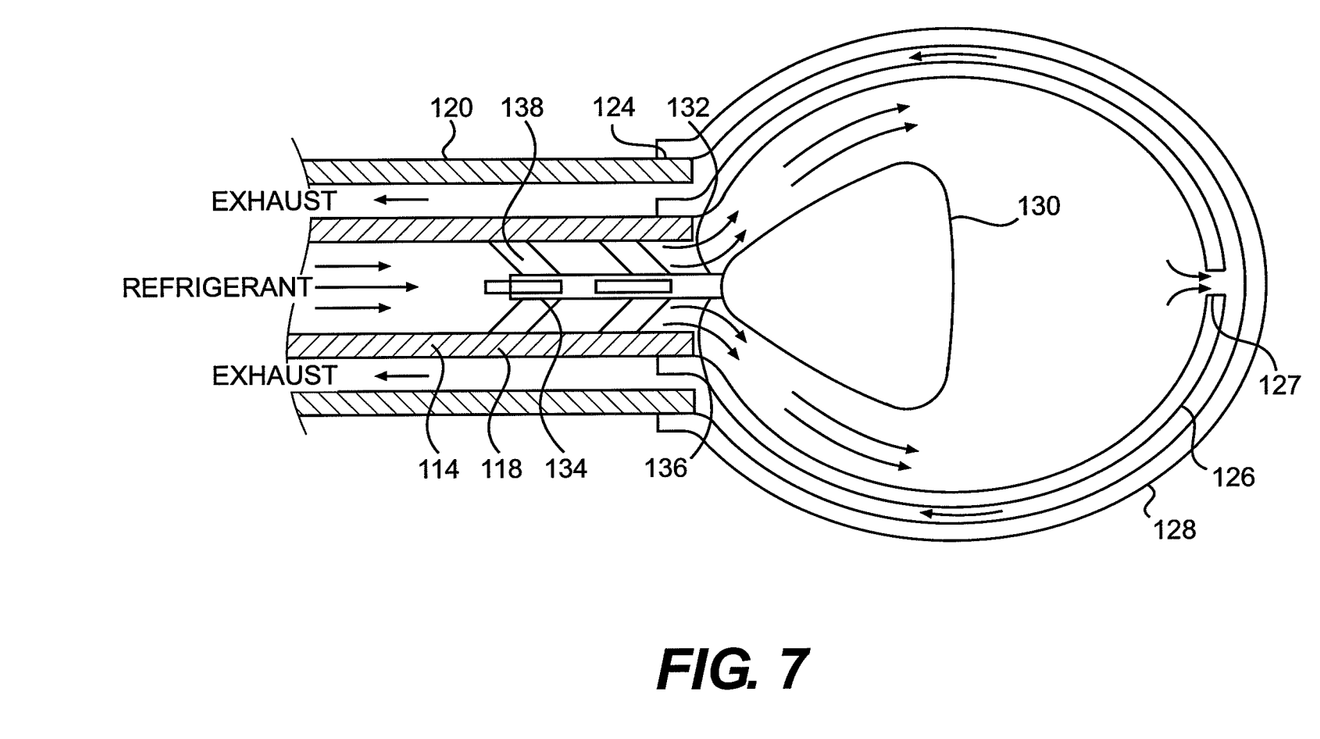
FIG. 7 is a cross-sectional side view of one embodiment of a cryoablation catheter disclosed herein.

Referring now to FIG. 7, another embodiment of the cyroablation catheter is depicted. In one aspect, a dispersion member 130 can reside within cyrochamber 126. In the embodiment depicted, dispersion member 130 resembles a pyramidal or conical body, narrow at the proximal end of cyrochamber 126 and widening out towards the mid-section of the chamber. However, in other embodiments, the shape of dispersion member 130, particularly the shape of the surface facing the distal end of supply lumen 114, can depend on the desired flow of the refrigerant within cyrochamber 126. For example, a less drastically tapering dispersion member can be used if it is desired that the refrigerant be directed towards the proximal end of the cyrochamber. Alternatively, a more drastically tapering dispersion member can be used if it is desired that the refrigerant be directed more towards the distal end of cyrochamber 126 or directed along the inner wall of the chamber rather than at the wall.

In the embodiment depicted, dispersion member 130 can be anchored in place within cyrochamber 126 through the use of stem 132 having a proximal end 134 and a distal end 136. In one aspect, distal end 136 of stem 132 can be coupled to dispersion member 130 while the proximal end 134 at least partially resides within distal end 118 or supply lumen 114. Protruding from distal end 136 of stem 132 can be fins 138 which contact the inner surface of supply lumen 114. In one embodiment, fins 138 can be affixed to the inner surface of lumen 114. In other embodiments, the fins and the supply lumen, along with stem 132 and dispersion member 130, can be manufactured as one piece. However, this is but one method of securing dispersion member 130 within cyrochamber 126. Various other methods of anchoring dispersion member 130 within the cyrochamber can be incorporated in alternative embodiments. For example, dispersion member could be affixed or built in to the distal wall of the cryochamber or could be affixed to a chamber wall, as shown in FIG. 3A or 3B.

In practice, a pressurized refrigerant or cyrofluid can be released from refrigerant supply unit 104, enter proximal end 116 of supply lumen 114, flow down to distal end 118 of the lumen, past fins 138 and into cyrochamber 126. Upon entering the cryochamber, dispersion member 130 can deflect the fluid toward the inner wall of the chamber. The deflection of the cyrofluid by dispersion member 130 can concentrate the refrigerant stream along the side walls of the cryochamber rather than the distal end of the cyrochamber.

In another aspect, the spent, or gaseous, refrigerant can then leave cyrochamber 126 through exit 127. In the embodiment depicted in FIG. 7, exit 127 is located at the distal end of the cyrochamber. In other embodiments, however, the exit can be located elsewhere within the chamber. The refrigerant leaving cyrochamber 126 can then be contained by exhaust chamber 128, which houses the cyrochamber. The spent cryofluid can then be allowed to flow into distal end 124 of exhaust lumen 120 and exit the system at proximal end 122 of the lumen. It should be noted, however, the exhaust of spent refrigerant can be accomplished in various ways. Additional methods of exhausting the gas are described above, though other methods can also be incorporated in different embodiments and the methods described herein should not be read to exclude other possible alternatives.

All the embodiments of the invention discussed above can be used to perform cyroablation of targeted tissue. A method of use can comprise the provision of one of the cyrocatheters described and delivering a refrigerant to the distal end of the device, into the cyrochamber where the refrigerant is directed by a dispersion member toward and/or along a desired portion of the inner wall(s) of the chamber.

Additional features can also be incorporated into the cryoablation catheter device to improve its functionality. For example, the components of the device can be comprised of a medical grade material suitable for a surgical environment or a radiopaque material so as to permit visualization of the catheter during the procedure. In other embodiments, force, pressure, strain, and/or temperature sensors can be incorporated into the device providing the surgeon with information about the refrigerant within the catheter and cyrochamber and the surrounding targeted tissue. Additionally, conductive materials can be placed or integrated into the inner surface of the cyrochamber and/or exhaust chamber to facilitate uniform cooling of the targeted tissue. Further, additional outer chambers can be used to house those discussed herein to moderate cooling and/or protect against rupture, breakage, and escape of the cryofluid.

The cyroablation catheter described herein can also be used to ablate tissue in other areas of the body aside from epicardial tissue. In fact, the device can be used in any ablative procedure that utilizes a cryochamber at the distal end of a catheter body.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A cryotherapy catheter device, comprising:
   an elongate catheter body having a longitudinal axis extending between a proximal end and a distal end;
   an expansion chamber adapted to receive a refrigerant from the distal end of the elongate catheter body; and
   a refrigerant dispersion member residing within the expansion chamber and configured to redirect the flow of the refrigerant away from a distal end of the expansion chamber and disperse the refrigerant across at least a portion of an interior surface of the expansion chamber, wherein the dispersion member is positioned such that refrigerant exiting the distal end of the elongate catheter body and flowing in a distal direction impacts the dispersion member before reaching the distal end of the expansion chamber, and is redirected by the dispersion member to a region of the expansion chamber away from the distal end.

2. The device of claim 1, wherein the refrigerant dispersion member directs the refrigerant in a radial direction.

3. The device of claim 1, wherein the refrigerant dispersion member directs the refrigerant around a full circumference of the expansion chamber.

4. The device of claim 1, wherein the refrigerant dispersion member directs the refrigerant around only a portion of a circumference of the expansion chamber.

5. The device of claim 1, wherein the dispersion member comprises a body rotatably coupled to the distal end of the elongate catheter.

6. The device of claim 5, wherein the dispersion member further comprises a first aperture for receiving a refrigerant from the distal end of the elongate catheter body and at least a second aperture for the refrigerant to exit the dispersion member within the expansion chamber.

7. The device of claim 6, wherein the dispersion member further comprises at least a third aperture for the refrigerant to exit the dispersion member within the expansion chamber.

8. The device of claim 1, wherein the dispersion member has at least one surface substantially in a plane perpendicular to the longitudinal axis of the elongate catheter at its distal end.

9. The device of claim 1, wherein the dispersion member includes a fluid contact surface with a convex shape.

10. The device of claim 1, wherein the dispersion member includes a fluid contact surface with a concave shape.

11. The device of claim 1, wherein the dispersion member has a surface positioned so as to redirect the flow of a refrigerant exiting the distal end of the elongate catheter body in a radial direction, with respect to the elongate catheter body.

12. The device of claim 1, wherein the dispersion member is anchored to the distal end of the elongate catheter body.

13. The device of claim 1, wherein the dispersion member is anchored to an inner wall of the expansion chamber.

14. The device of claim 1, wherein the dispersion member is configured to disperse the refrigerant along a portion that is concentric with the elongate catheter body.

15. The device of claim 1, wherein the dispersion member comprises an opening in fluid communication with the distal end of the elongate catheter body and a plurality of apertures in fluid communication with the expansion chamber.

16. A cryotherapy catheter device, comprising:
an elongate catheter body having a longitudinal axis extending between a proximal end and a distal end;
an expansion chamber adapted to receive a flow of refrigerant from the distal end of the elongate catheter body; and
a refrigerant dispersion member residing within the expansion chamber and configured to deflect the flow of the refrigerant away from an axial direction and towards a radial direction within the expansion chamber, wherein the dispersion member is positioned distal of the distal end of the elongate catheter body and positioned such that it alters the flow direction of refrigerant before the refrigerant reaches the distal end of the expansion chamber.

17. The cryotherapy catheter device of claim 16, wherein the refrigerant dispersion member is connected to the distal end of the elongate catheter body.

18. The cryotherapy catheter device of claim 17, wherein the refrigerant dispersion member is in fluid communication with the elongate catheter body.

19. The cryotherapy catheter device of claim 16, wherein the refrigerant dispersion member is configured to concentrate the flow of refrigerant along a circumferential band on an inner wall of the expansion chamber.

20. A cryotherapy catheter device, comprising:
an elongate catheter body having a longitudinal axis extending between a proximal end and a distal end;
an expansion chamber adapted to receive a flow of refrigerant from the distal end of the elongate catheter body; and
a refrigerant dispersion member residing within the expansion chamber and configured such that when the refrigerant reaches the dispersion member, the dispersion member changes the direction of flow of the refrigerant away from a distal end of the expansion chamber and towards a sidewall of the expansion chamber.

21. The cryotherapy catheter device of claim 20, wherein the refrigerant dispersion member is connected to a distal region of the elongate catheter body.

22. The cryotherapy catheter device of claim 20, wherein the dispersion member has a conical body having a tip positioned proximally within the expansion chamber.

23. The cryotherapy catheter device of claim 20, wherein the dispersion member is configured to concentrate the flow of the refrigerant along the sidewall of the expansion chamber.

* * * * *